(12) United States Patent
Wang et al.

(10) Patent No.: US 7,395,249 B2
(45) Date of Patent: *Jul. 1, 2008

(54) SPEECH INTERFACE FOR AN AUTOMATED ENDOSCOPE SYSTEM

(75) Inventors: Yulun Wang, Goleta, CA (US); Darrin Uecker, Santa Barbara, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/942,374

(22) Filed: Sep. 15, 2004

(65) Prior Publication Data

US 2005/0033580 A1      Feb. 10, 2005

Related U.S. Application Data

(63) Continuation of application No. 10/095,488, filed on Mar. 11, 2002, now Pat. No. 6,965,812, which is a continuation of application No. 08/310,665, filed on Sep. 22, 1994, now Pat. No. 6,463,361.

(51) Int. Cl.
*G06F 15/18* (2006.01)
*G06F 15/00* (2006.01)
*G10L 11/00* (2006.01)

(52) U.S. Cl. .......................................... 706/14; 704/200
(58) Field of Classification Search ................. 700/258, 700/245, 264; 606/130, 425; 128/897; 704/246; 600/425; 706/14
See application file for complete search history.

(56) References Cited

U.S. PATENT DOCUMENTS

| | | | |
|---|---|---|---|
| 977,825 A | 12/1910 | Murphy | |
| 3,171,549 A | 3/1965 | Orloff | |
| 3,280,991 A | 10/1966 | Melton et al. | |
| 3,300,053 A * | 1/1967 | Peters | 210/519 |
| 4,058,001 A | 11/1977 | Waxman | |
| 4,128,880 A | 12/1978 | Cray, Jr. | |
| 4,158,750 A * | 6/1979 | Sakoe et al. | 704/251 |
| 4,207,959 A | 6/1980 | Youdin et al. | |
| 4,216,462 A | 8/1980 | McGrath et al. | |
| 4,221,997 A | 9/1980 | Flemming | |
| 4,340,800 A * | 7/1982 | Ueda et al. | 219/714 |
| 4,348,553 A * | 9/1982 | Baker et al. | 704/241 |
| 4,367,998 A | 1/1983 | Causer | |
| 4,401,852 A | 8/1983 | Noso et al. | |

(Continued)

FOREIGN PATENT DOCUMENTS

DE    9204118.3    7/1992

(Continued)

OTHER PUBLICATIONS

Voice control in the surgery room Guerrouad, A.; Engineering in Medicine and Biology Society, 1989. Images of the Twenty-First Century. Proceedings of the Annual International Conference of the IEEE Engineering in Nov. 9-12, 1989 pp. 904-905 vol. 3 Digital Object Identifier 10.1109/IEMBS.1989.96040.*

(Continued)

*Primary Examiner*—Michael B. Holmes

(57) ABSTRACT

A robotic system which controls the movement of a surgical instrument in response to voice commands from the user. The robotic system has a computer controlled arm that holds the surgical instrument. The user provides voice commands to the computer through a microphone. The computer contains a phrase recognizer that matches the user' speech with words stored in the computer. Matched words are then processed to determine whether the user has spoken a robot command. If the user has spoken a recognized robot command the computer will move the robotic arm in accordance with the command.

26 Claims, 3 Drawing Sheets

U.S. PATENT DOCUMENTS

| | | | |
|---|---|---|---|
| 4,454,586 A * | 6/1984 | Pirz et al. | 704/245 |
| 4,456,961 A | 6/1984 | Price et al. | |
| 4,460,302 A | 7/1984 | Moreau et al. | |
| 4,472,617 A * | 9/1984 | Ueda et al. | 219/723 |
| 4,474,174 A | 10/1984 | Petruzzi | |
| 4,482,032 A * | 11/1984 | Enriquez et al. | 187/392 |
| 4,491,135 A | 1/1985 | Klein | |
| 4,503,854 A | 3/1985 | Jako | |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,605,080 A * | 8/1986 | Lemelson | 177/4 |
| 4,616,637 A | 10/1986 | Caspari et al. | |
| 4,624,002 A | 11/1986 | Zahalka et al. | |
| 4,624,008 A * | 11/1986 | Vensko et al. | 704/253 |
| 4,624,011 A | 11/1986 | Watanabe et al. | |
| 4,633,389 A | 12/1986 | Tanaka et al. | |
| 4,633,499 A * | 12/1986 | Nishioka et al. | 704/253 |
| 4,635,292 A | 1/1987 | Mori et al. | |
| 4,641,292 A * | 2/1987 | Tunnell et al. | 367/198 |
| 4,655,257 A | 4/1987 | Iwashita | |
| 4,672,963 A | 6/1987 | Barken | |
| 4,676,243 A | 6/1987 | Clayman | |
| 4,717,364 A * | 1/1988 | Furukawa | 446/175 |
| 4,725,956 A * | 2/1988 | Jenkins | 701/2 |
| 4,728,974 A | 3/1988 | Nio et al. | |
| 4,750,136 A | 6/1988 | Arpin | |
| 4,757,541 A * | 7/1988 | Beadles | 704/254 |
| 4,762,455 A | 8/1988 | Coughlan et al. | |
| 4,776,016 A * | 10/1988 | Hansen | 704/275 |
| 4,791,934 A | 12/1988 | Brunnett | |
| 4,791,940 A | 12/1988 | Hirschfeld | |
| 4,794,912 A | 1/1989 | Lia | |
| 4,797,924 A * | 1/1989 | Schnars et al. | 704/275 |
| 4,799,171 A * | 1/1989 | Cummings | 704/272 |
| 4,805,219 A * | 2/1989 | Baker et al. | 704/241 |
| 4,807,273 A | 2/1989 | Haendle | |
| 4,815,006 A | 3/1989 | Andersson et al. | |
| 4,815,450 A | 3/1989 | Patel | |
| 4,817,050 A | 3/1989 | Komatsu | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnel | |
| 4,883,400 A | 11/1989 | Kuban et al. | |
| 4,898,253 A | 2/1990 | Oldendorf et al. | |
| 4,903,304 A * | 2/1990 | Schlang et al. | 704/253 |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,218,969 A * | 6/1993 | Bredesen et al. | 600/523 |
| 5,221,283 A | 6/1993 | Chang | |
| 5,228,429 A | 7/1993 | Hatano | |
| 5,230,023 A | 7/1993 | Nakano | |
| 5,230,623 A | 7/1993 | Guthrie et al. | |
| 5,236,432 A | 8/1993 | Matsen, III et al. | |
| 5,249,121 A | 9/1993 | Baum et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,274,862 A | 1/1994 | Palmer, Jr. et al. | |
| 5,279,309 A | 1/1994 | Taylor et al. | |
| 5,282,806 A | 2/1994 | Haber | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,303,882 A | 4/1994 | Bandyopadhyay | |
| 5,304,185 A | 4/1994 | Taylor | |
| 5,305,203 A | 4/1994 | Raab | |
| 5,305,244 A | 4/1994 | Newman et al. | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,335,313 A | 8/1994 | Douglas | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamagushi | |
| 5,372,147 A | 12/1994 | Lathrop, Jr. et al. | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A * | 4/1995 | Colgate et al. | 700/264 |
| 5,417,210 A * | 5/1995 | Funda et al. | 600/425 |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,436,542 A | 7/1995 | Petelin et al. | |
| 5,442,728 A | 8/1995 | Kaufman et al. | |
| 5,443,384 A | 8/1995 | Kirsch at al. | |
| 5,445,166 A | 8/1995 | Taylor | |
| 5,451,924 A | 9/1995 | Massimino et al. | |
| 5,455,766 A | 10/1995 | Schaller et al. | |
| 5,458,547 A | 10/1995 | Teraoka et al. | |
| 5,458,574 A | 10/1995 | Machold et al. | |

| | | |
|---|---|---|
| 5,476,010 A | 12/1995 | Fleming et al. |
| 5,490,117 A | 2/1996 | Oda |
| 5,490,843 A | 2/1996 | Hildwein et al. |
| 5,500,854 A | 3/1996 | Uotila |
| 5,506,912 A | 4/1996 | Nagasaki et al. |
| 5,511,256 A | 4/1996 | Capaldi |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,566,272 A | 10/1996 | Brems et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,622,730 A * | 4/1997 | Nitta et al. ............ 425/141 |
| 5,626,595 A | 5/1997 | Sklar et al. |
| 5,627,584 A | 5/1997 | Nishikori et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,640,953 A | 6/1997 | Bishop et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A * | 12/1997 | Taylor et al. ............ 606/130 |
| 5,696,574 A | 12/1997 | Schwaegerle |
| 5,696,837 A | 12/1997 | Green |
| 5,707,942 A * | 1/1998 | Arai et al. ............ 508/365 |
| 5,713,350 A | 2/1998 | Yokota et al. |
| 5,715,548 A | 2/1998 | Weismiller et al. |
| 5,715,823 A | 2/1998 | Wood |
| 5,718,038 A | 2/1998 | Takiar et al. |
| 5,727,569 A | 3/1998 | Benetti et al. |
| 5,729,659 A | 3/1998 | Potter |
| 5,735,290 A | 4/1998 | Sterman et al. |
| 5,737,711 A | 4/1998 | Abe |
| 5,749,362 A | 5/1998 | Fund et al. |
| 5,754,741 A | 5/1998 | Wang et al. |
| 5,758,021 A * | 5/1998 | Hackbarth ............ 704/232 |
| 5,762,458 A | 6/1998 | Wang et al. |
| 5,771,511 A | 6/1998 | Kummer et al. |
| 5,774,741 A | 6/1998 | Choi |
| 5,774,841 A | 6/1998 | Salazar et al. |
| 5,776,126 A | 7/1998 | Wilk et al. |
| 5,779,623 A | 7/1998 | Bonnell |
| 5,788,688 A | 8/1998 | Bauer et al. |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,802,467 A | 9/1998 | Salazar et al. |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,809,591 A | 9/1998 | Capaldi et al. |
| 5,810,880 A | 9/1998 | Jensen et al. |
| 5,812,978 A | 9/1998 | Nolan |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,841,950 A | 11/1998 | Wang et al. |
| 5,842,173 A | 11/1998 | Strum et al. |
| 5,844,824 A | 12/1998 | Newman et al. |
| 5,855,583 A | 1/1999 | Wang et al. |
| 5,857,967 A | 1/1999 | Frid et al. |
| 5,859,934 A | 1/1999 | Green |
| 5,860,995 A | 1/1999 | Berkelaar |
| 5,868,675 A | 2/1999 | Henrion et al. |
| 5,876,325 A | 3/1999 | Mizuno et al. |
| 5,877,819 A | 3/1999 | Branson |
| 5,878,193 A | 3/1999 | Wang et al. |
| 5,882,206 A | 3/1999 | Gillio |
| 5,884,350 A | 3/1999 | Kurze |
| 5,887,121 A | 3/1999 | Funda et al. |
| 5,895,461 A | 4/1999 | De La Huerga |
| 5,897,498 A | 4/1999 | Canfield et al. |
| 5,924,074 A | 7/1999 | Evans |
| 5,931,832 A | 8/1999 | Jensen |
| 5,950,629 A * | 9/1999 | Taylor et al. ............ 128/897 |
| 5,970,457 A | 10/1999 | Brant et al. |
| 5,971,976 A | 10/1999 | Wang et al. |
| 5,976,156 A * | 11/1999 | Taylor et al. ............ 606/130 |
| 5,995,930 A * | 11/1999 | Hab-Umbach et al. ...... 704/254 |
| 6,024,695 A | 2/2000 | Taylor et al. |
| 6,080,181 A | 6/2000 | Jensen et al. |
| 6,102,850 A | 8/2000 | Wang et al. |
| 6,201,984 B1 | 3/2001 | Funda et al. |
| 6,224,542 B1 | 5/2001 | Chang et al. |
| 6,278,975 B1 | 8/2001 | Brant et al. |
| 6,463,361 B1 * | 10/2002 | Wang et al. ............ 700/258 |
| 6,496,099 B2 | 12/2002 | Wang et al. |
| 6,642,836 B1 | 11/2003 | Wang et al. |
| 6,646,541 B1 | 11/2003 | Wang et al. |
| 6,788,999 B2 | 9/2004 | Green |
| 6,850,817 B1* | 2/2005 | Green ............ 700/245 |
| 6,911,916 B1 | 6/2005 | Wang et al. |
| 6,943,663 B2 | 9/2005 | Wang et al. |
| 6,965,812 B2 | 11/2005 | Wang et al. |
| 7,053,752 B2 | 5/2006 | Wang et al. |
| 7,097,640 B2 | 8/2006 | Wang et al. |
| 7,259,652 B2 | 8/2007 | Wang et al. |
| 2002/0140665 A1 | 10/2002 | Gordon |
| 2005/0154288 A1 | 7/2005 | Wang et al. |
| 2006/0220784 A1 | 10/2006 | Wang et al. |
| 2006/0241575 A1 | 10/2006 | Wang et al. |

FOREIGN PATENT DOCUMENTS

| | | |
|---|---|---|
| DE | 4310842 | 1/1995 |
| EP | 0239409 | 9/1987 |
| EP | 0424687 | 5/1991 |
| EP | A-0494943 | 8/1995 |
| EP | 0776738 | 6/1997 |
| FR | 2 642 882 | 8/1990 |
| JP | 62-103242 | 5/1987 |
| JP | 09-248279 | 9/1997 |
| JP | 09-248297 | 9/1997 |
| WO | 91/04711 | 4/1991 |
| WO | WO 91/11766 | 8/1991 |
| WO | 92/20295 | 11/1992 |
| WO | 93/13916 | 7/1993 |
| WO | 94/18881 | 9/1994 |
| WO | 94/26167 | 11/1994 |
| WO | WO 95/01757 * | 1/1995 |
| WO | 96/09587 | 3/1996 |
| WO | 97/15240 | 5/1997 |
| WO | WO97/15240 | 5/1997 |
| WO | 98/25666 | 6/1998 |
| WO | 99/21165 | 4/1999 |
| WO | 99/42029 | 8/1999 |

OTHER PUBLICATIONS

Automatic analysis of weariness during a micromanipulation task by SMOSGuerrouad, A.; Jolly, D.; Engineering in Medicine and Biology Society, 1989. Images of the Twenty-First Century. Proceedings of the Annual International Conference of the IEEE Engineering in Nov. 9-12, 1989 pp. 906-907 vol. 3 Digital Object Identifier 10.1109/IEMBS.1989.96.*

SMOS: stereotaxical microtelemanipulator for ocular surgery Guerrouad, A.; Vidal, P.; Engineering in Medicine and Biology Society, 1989. Images of the Twenty-First Century. Proceedings of the Annual International Conference of the IEEE Engineering in Nov. 9-12, 1989 pp. 879-880 vol. 3 Digital Object Identifier 10.1109/IEMBS.1989.96028.*

Advantage of computer aided teleoperation (CAT) in microsurgery Guerrouad, A.; Vidal, P.; Advanced Robotics, 1991. 'Robots in Unstructured Environments', 91 ICAR., Fifth International Conference on Jun. 19-22, 1991 pp. 910-914 vol. 1 Digital Object Identifier 10.1109/ICAR.1991.240557.*

Abstract of a presentation "3-D Vision Technology Applied to Advanced Minimally Invasive Surgery Systems" given at the 3rd World Congress of Endoscopic Surgery in Bordeaux, Jun. 18-20, 1992 (1 page total).

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

Abstract of a presentation "Concept and Experimental Application of a Surgical Robot System and Steerable MIS Instrument SMI" given at the 3rd World Congress of Endoscopic Surgery in Bordeaux, Jun. 18-29, 1992 (1 page total).

Abstract of a presentation given at the 3rd World Congress of Endoscopic Surgery in Bordeaux (Jun. 18-20, 1992), entitled "Session 15/2" (1 page total).

Abstract of a presentation given at the 3rd World Congress of Endoscopic Surgery in Bordeaux (Jun. 18-20, 1992), entitled "Session 15/4" (1 page total).

Abstract of a presentation given at the 3rd World Congress of Endoscopic Surgery in Bordeaux (Jun. 18-20, 1992), entitled "Session 15/5" (1 page total).

Abstract of a presentation given at the 3rd World Congress of Endoscopic Surgery in Bordeaux, Jun. 18-20, 1992, entitled "Session 15/1" (1 page total).

Alexander, "A Survey Study of Teleoperators, Robotics, and Remote Systems Technology", Remotely Manned Systems—Exploration and Operation in Space, California Institute of Technology 1973.

Alexander, "Impacts of Telemation on Modern Society", On the Theory and Practice of Robots and Manipulators vol. II, 1974.

Bejczy, "Controlling Remote Manipulators through Kinesthetic Coupling," Computers in Mechanical Engineering 1983, pp. 48-60.

Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Fu et al., "Robotics: Control, Sensing, Vision and Intelligence", Table of Contents, McGraw—Hill Book Company, 1987.

Gayed et al., "An Advanced Control Micromanipulator for Surgical Applications," Systems Science vol. 13, 1987, pp. 23-24.

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Green, Statutory Declaration of Dr. Philip S. Green, presenter of the video entitled "Telepresence Surgery—The Future of Minimally Invasive Medicine" (32 page total).

Guerrouad et al., "S.M.O.S.: Stereotaxical Microtelemanipulator for Ocular Surgery," IEEE, 1989, pp. 879-880.

Guerrouad, "Voice Control in the Surgery Room," IEEE Engineering in Medicine & Biology Society 11th Annual International Conference 1989 (2 pages total).

Inoue et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

Majima et al., "On a Micro-Manipulator for Medical Application—Stability Consideration of its Bilateral Controller," Mechatronics, 1991, pp. 293-309.

Nasa, "Anthropomorphic Remote Manipulator", NASA Tech Briefs, 1991 (1 page total).

Preising et al., "A Literature Review: Robots in Medicine," IEEE, Jun. 1991, pp. 13-22 & 71.

Rasor et al., "Endocorporeal Surgery Using Remote Manipulators", Remotely Manned Systems—Exploration and Operation in Space, California Institute of Technology 1973.

Sabatini et al., "Force Feedback-Based Telemicromanipulation for Robot Surgery on Soft Tissues," IEEE, 1989, pp. 890-891.

Stryker Endoscopy, "Sidne", Operating and Maintenance Manual, 33 pages total.

Taubes, "Surgery in Cyberspace," Discover Magazine, Dec. 1994, pp. 85-92.

Taylor et al., "Taming the Bull: Safety in a Precise Surgical Robot," IEEE, 1991, pp. 865-871.

Tejima, "A New Microsurgical Robot System for Corneal Transplantation," Precision Machinery, 1988 vol. 2, pp. 1-9.

Tendick et al., "Analysis of the Surgeon's Grasp for Telerobotic Surgical Manipulation," IEEE, 1989, pp. 914-915.

Thring, "Robots and Telechirs: Manipulator with Memory: Remote Manipulators: Machine Limbs for the Handicapped," Wiley & Sons, 1983 (26 pages total).

Transcript of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled "Telepresence Surgery—The Future of Minimally Invasive Medicine" (3 pages total).

Trevelyan et al., "Motion Control for a Sheep Shearing Robot," Proceedings of the 1st International Symposium on Robotics Research, MIT, Cambridge, Massachusetts, USA, 1983, pp. 175.

Vibet, "Properties of Master-Slave Robots," Motor-con, 1987, pp. 309-314.

Wilson et al., "Filmless PACS in a multiple facility environment," Proceedings of the Spie, Spie, Bellingham, VA, US vol. 2711, pp. 500-509 (XP002082137).

Wolf et al., "Student Reference Manual for Electronic Instrumentation Laboratories," Prentice Hall, New Jersey 1990, pp. 498 and 499.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

Rasor et al., "Endocorporeal Surgery Using Remote Manipulators", Remotely Manned Systems—Exploration and Operation in Space, California Institute of Technology 1973.

* cited by examiner

SPEECH INTERFACE FOR AN AUTOMATED ENDOSCOPE SYSTEM

CROSS-REFERENCE TO RELATED APPLICATION

This is a continuation of U.S. patent application Ser. No. 10/095,488 filed Mar. 11, 2002, the full disclosure of which is incorporated herein by reference, which is a continuation U.S. patent application Ser. No. 08/310,665 filed on Sep. 22 1994.

BRIEF SUMMARY OF THE INVENTION

The present invention is a robotic system which controls the movement of a surgical instrument in response to voice commands from the user. A surgical instrument is a tool or device used during a surgery or operation. Examples of surgical instruments include forceps, laparoscopes, endoscopes, and medical telescopes. The robotic system has a computer controlled arm that holds the surgical instrument. The user provides voice commands to the computer through a microphone. The computer contains a phrase recognizer that matches the user's speech with words stored in the computer. Matched words are then processed to determine whether the user has spoken a robot command. If the user has spoken a recognized robot command the computer will move the robotic arm in accordance with the command.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
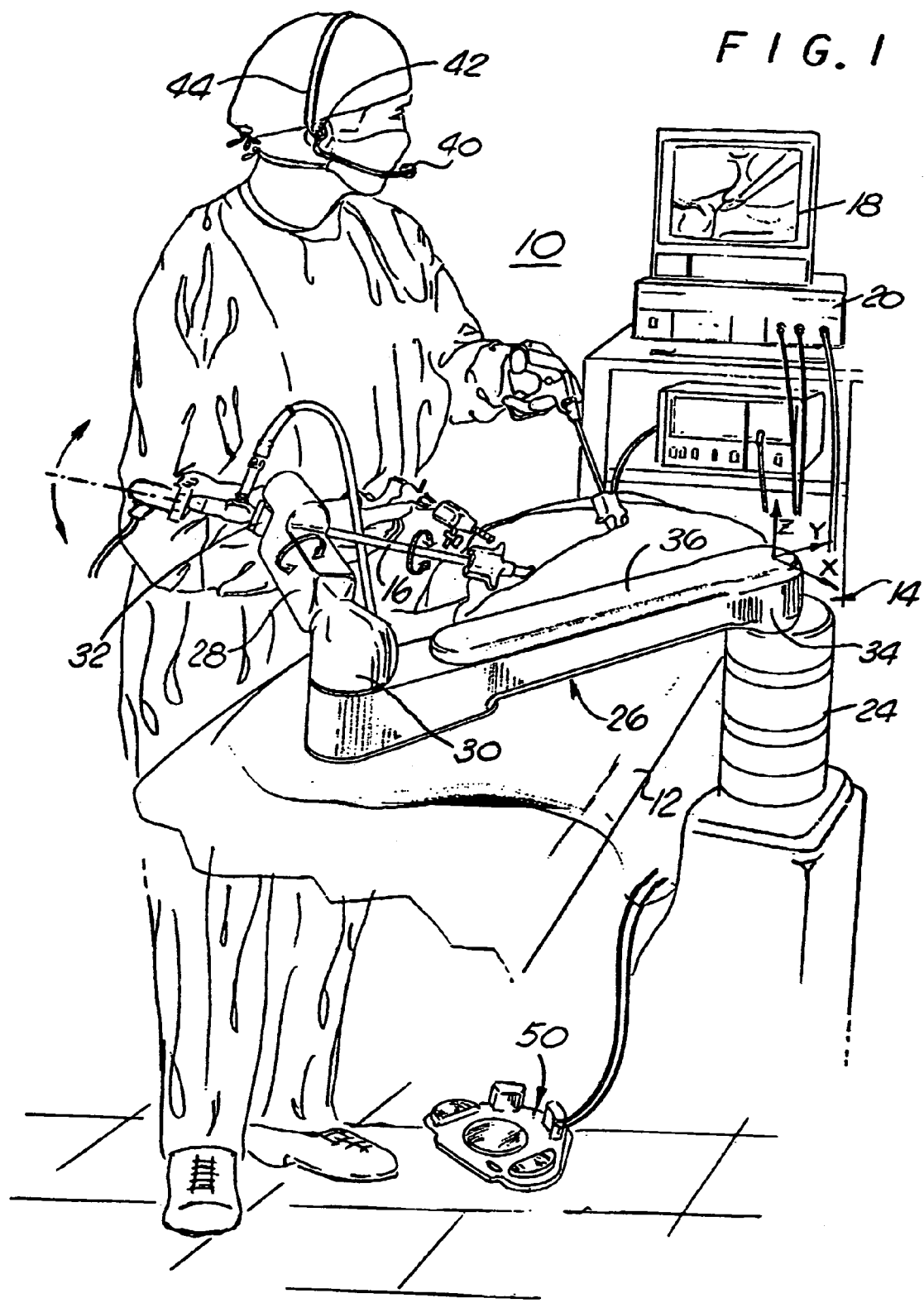
FIG. 1 is a perspective view of a robotic endoscope system of the present invention.

Referring to the drawings more particularly by reference numbers, FIG. 1 shows a robotic system 10 of the present invention. The system 10 is typically used in a sterile operating room where a surgeon performs a surgical procedure on a patient. The patient is placed on a operating table 12. Attached to the table 12 is a robotic arm assembly 14 which can move a surgical instrument 16 relative to the table 12 and the patient. The surgical instrument 16 is typically an endoscope which is inserted into the abdomen of the patient 12. The endoscope 16 enters the patient through a cannula, wherein the scope 16 rotate about a cannula pivot point. The endoscope is typically connected to a monitor 18 which allows the surgeon to view the organs, etc. of the patient. Although an endoscope is described and shown, it is to be understood that the present invention can be used with other surgical instruments.

The robotic arm assembly 14 controlled by a computer 20. In the preferred embodiment, the robotic arm assembly 16 includes a linear actuator 24 fixed to the table 14. The linear actuator 24 is connected to a linkage arm assembly 26 and adapted to move the linkage assembly 26 along the z axis of a first coordinate system. The first coordinate system also has an x axis and a y axis.

Figure 2:
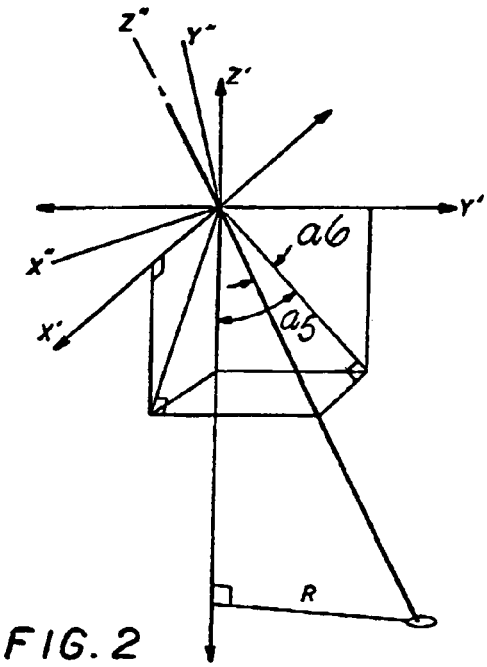
FIG. 2 is a schematic of an endoscope within two separate coordinate systems.

The linkage arm assembly 26 includes a first linkage arm 28 attached to a first rotary actuator 30 and an end effector 32. The first rotary actuator 30 is adapted to rotate the first linkage arm 28 and end effector 32 in a plane perpendicular to the z axis (x-y plane) The first rotary actuator 30 is connected to a second rotary actuator 34 by a second linkage arm 36. The second actuator 34 is adapted to rotate the first actuator 30 in the x-y plane. The second rotary actuator 34 is connected to the output shaft of the linear actuator 24. The actuators 24, 30 and 34 rotate in response to output signals provided by the computer 20. As shown in FIG. 2, the junction of the endoscope 16 and the end effector 32 define a second coordinate-system which has an x' axis, a y' axis and a z' axis. The junction of the end effector 32 and endoscope 18 also define the origin of a third coordinate system which has a x' axis, a p axis and a z'' axis. The z'' axis parallel with the longitudinal axis of the endoscope 16.

The arm assembly may have a pair of passive joints that allow the end effector to be rotated in the direction indicated by the arrows. The actuators 24, 30 and 34, and joints of the arm may each have position sensors (not shown) that are connected to the computer 20. The sensors provide positional feedback signals of each corresponding arm component.

The system has a microphone 40 that is connected to the computer 20. The system may also have a speaker 42 that is connected to the computer 20. The microphone 40 and speaker 42 may be mounted to a headset 44 that is worn by the user. Placing the microphone 40 in close proximity to the user reduces the amount of background noise provided to the computer and decreases the probability of an inadvertent input command.

Figure 3:
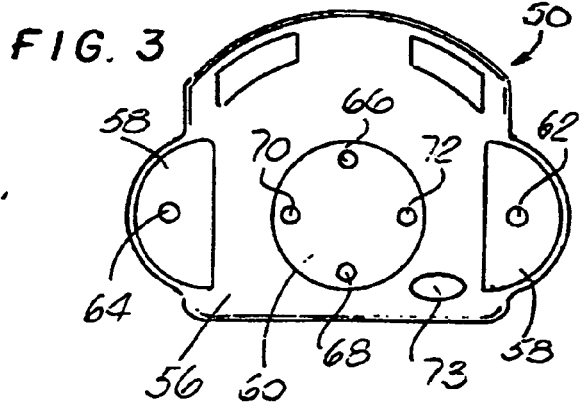
FIG. 3 is a top view of a foot pedal.

As shown in FIG. 3, the system may also have a foot pedal 50. The foot pedal 22 has a housing 56 that supports a pair of outer first foot switches 58 and a second foot switch 60. One outer foot switch 58 has a first pressure transducer 62 and the other switch has a second pressure transducer 64. The second foot switch 60 has third 66, fourth 68, fifth 70 and sixth 72 pressure transducers. The transducers are each connected to a corresponding operational amplifier that provides a voltage input to the computer 20. The pressure transducers 62-72 are preferably constructed so that the resistance of each transducer decreases as the surgeon increases the pressure on the foot switches. Such a transducer is sold by Interlink Electronics. The decreasing transducer resistance increases the input voltage provided to the computer 20 from the operational amplifier. Each transducer corresponds to a predetermined direction within the image displayed by the monitor. In the preferred embodiment, the first pressure transducer 62 corresponds to moving the endoscope toward the image viewed by the surgeon. The second transducer 64 moves the scope away from the image. The third 66 and fourth 68 transducers move the image "up" and "down", respectively, and the fifth 70 and sixth 72 transducers move the image "left" and "right", respectively. The pedal may have a button 73 that enables the foot pedal 50 and disable the voice command feature, or vice versa.

Figure 4:
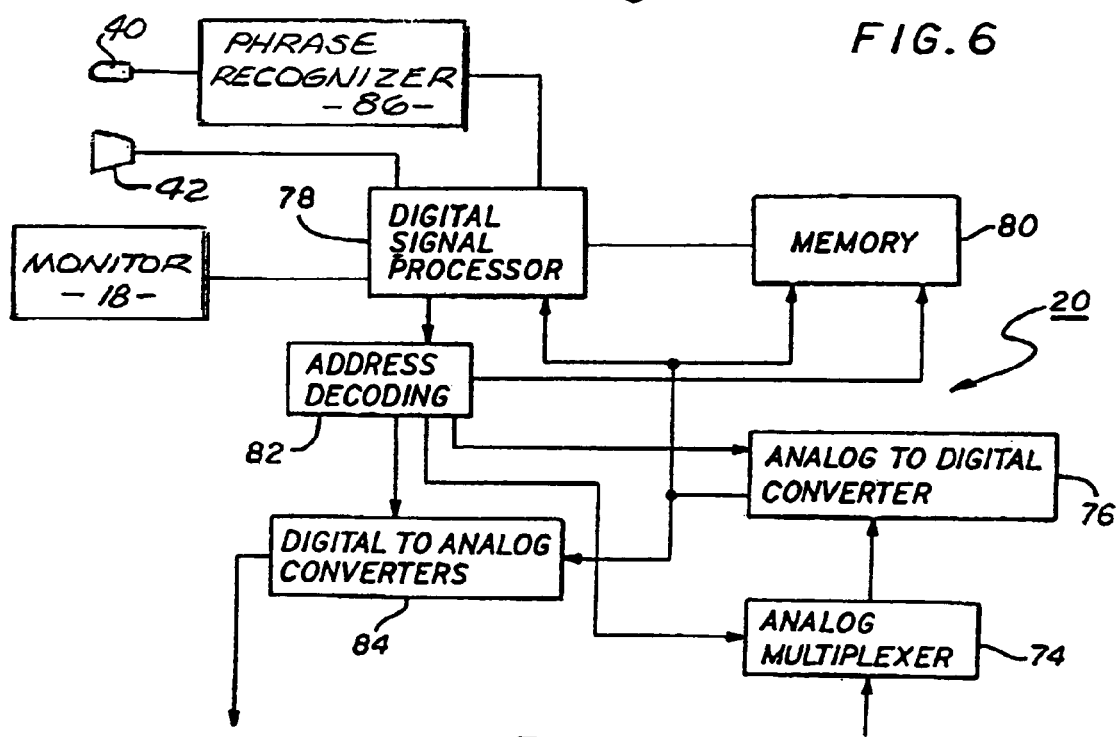
FIG. 4 is a schematic of a computer system.

FIG. 4 shows a schematic of the computer 20. The computer 20 has a multiplexer 74 which is connected to the pressure transducers of the foot pedal 50 and the position sensors of the arm. The multiplexer 74 is connected to a single analog to digital (A/D) converter 76. The computer 20 also has a processor 78 and memory 80.

The processor 78 is connected to an address decoder 82 and separate digital to analog (D/A) converters 84. Each D/A converter is connected to an actuator 24, 30 and 34. The D/A converters 84 provide analog output signals to the actuators in response to output signals received from the processor 78. The analog output signals have a sufficient voltage level to energize the electric motors and move the robotic arm assembly. The decoder 82 correlates the addresses provided by the processor with a corresponding D/A converter, so that the correct motor(s) is driven. The address decoder 82 also provides an address for the input data from the A/D converter 76 so that the data is associated with the correct input channel.

The computer 20 has a phrase recognizer 86 connected to the microphone 40 and the processor 78. The phrase recognizer 86 digitizes voice commands provided by the user through the microphone 40. The voice commands are then processed to convert the spoken words into electronic form. The electronic words are typically generated by matching the user's speech with words stored within the computer 20. In the preferred embodiment, the recognizer 86 is an electronic board with accompanying software that is marketed by SCOTT INSTRUMENTS of Denton, Tex. under the trademark "Coretechs Technology".

The electronic words are provided to the processor 78. The processor 78 compares a word, or a combination of words to predefined robot commands that are stored within a library in the memory 80 of the computer 20. If a word, or combination of words match a word or combination of words in the library, the processor 78 provides output commands to the D/A converter 84 to move the robotic arm in accordance with the command.

Figure 5:
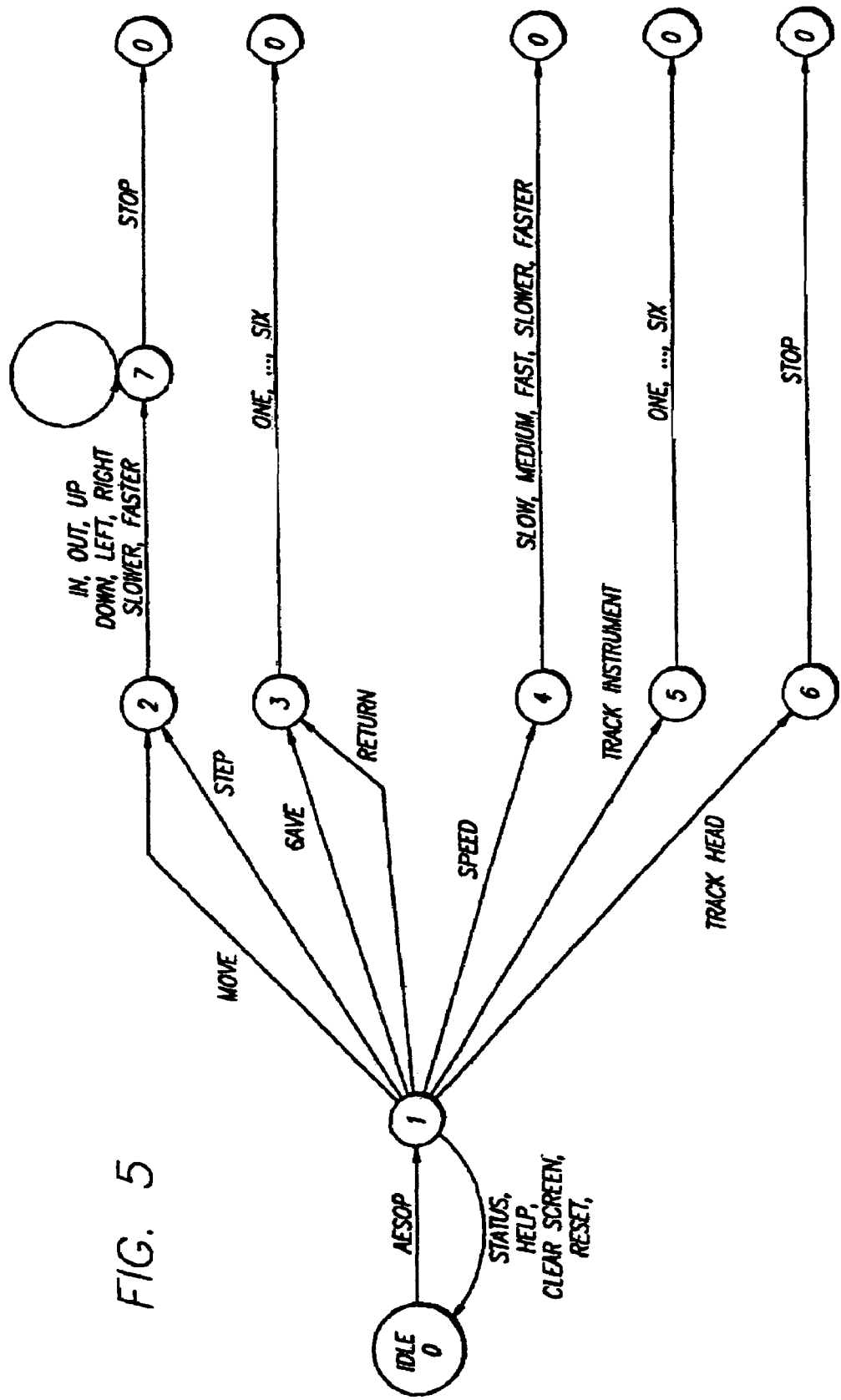
FIG. 5 is a schematic of a grammar process.

FIG. 5 shows exemplary words and combinations of words that provide robot commands. A grammar process is performed to determine whether the voice commands satisfy certain conditions. The process contains a number of states advanced by the satisfaction of a condition. If the voice command provided by the user satisfies a first condition, then the process proceeds to the first state. If a condition of a next state is satisfied then the process proceeds to the next corresponding state, and so forth and so on. For example, to prevent a robot command from being inadvertently spoken, it is desirable to predicate all voice commands with a qualifier. For example, the qualifier may be a name given to the robot such as "AESOP". Therefore when the user provides a voice command, the process initially determines whether the spoken word is AESOP. If the spoken word is not AESOP then the process ends. The term "stop" may be an exception to this rule, wherein the computer will stop arm movement when the user provides a simple "stop" voice command.

If the spoken word is AESOP the process continues to state 1. The process next determines whether the user has spoken a word that satisfies a condition to advance to states 2-6. These words include "move", "step", "save", "return", "speed", "track instrument" and "track head". The track instrument command is for a system which has the ability to move an endoscope to automatically track the movement of a second instrument that is inserted into the patient. The track head command may enable the system so that the endoscope movement tracks the user's eyes. For example, if the user looks to the right of the image displayed by the monitor, the robot will move the endoscope to move the image in a rightward direction. The move and step commands induce movement of the scope in a desired direction. The save command saves the position of the endoscope within the memory of the computer. The return command will return the scope to a saved position.

From states 2-6 the process will determine whether the user has spoken words that meet the next condition and so forth and so on. When a certain number of conditions have been met, the processor 78 will provide an output command to the D/A converter 84 in accordance with the voice commands. For example, if the user says "AESOP move left", the processor 78 will provide output commands to move the endoscope 12, so that the image displayed by the monitor moves in a leftward direction. The microphone 40 phrase recognizer 86 and grammar process essentially provide the same input function as the foot pedal 50, multiplexer 74 and A/D converter 76.

The processor 78 can also provide the user with feedback regarding the recognized command through the speaker 42 or the monitor 18. For example, when the user states "AESOP move right", after processing the speech, the processor 78 can provide an audio message through the speaker 42, or a visual message on the monitor 18, "AESOP move right". Additionally, the processor 78 can provide messages regarding system errors, or the present state of the system such as "speed is set for slow".

Figure 6:
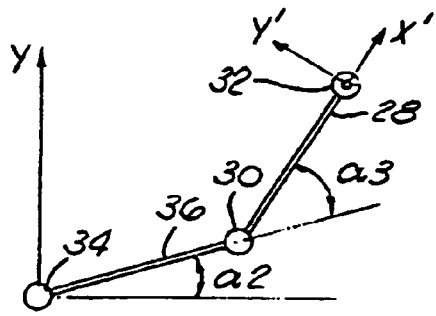
FIG. 6 is a schematic of a robotic arm.

Referring to FIG. 6, the processor 78 typically computes the movement of the robotic arm assembly 16 in accordance with the following equations.

$$a3 = \pi - \cos^{-1}\left(\frac{x^2 + y^2 - L1^2 + L2^2}{-2L1L2}\right) \quad 1)$$

$$\Delta = \cos^{-1}\left(\frac{x^2 + y^2 + L1^2 - L2^2}{2 \cdot L1\sqrt{x^2 + y^2}}\right)$$

$$a0 = \tan^{-1} 2\left(\frac{y}{x}\right)$$

$$a2 = a0 + /-\Delta$$

where;

a2=angle between the second linkage arm 36 and the x axis.

a3=angle between the first linkage arm 28 and the longitudinal axis of the second linkage arm 36.

L1=length of the second linkage arm.

L2=length of the first linkage arm.

x=x coordinate of the end effector in the first coordinate system.

y=y coordinate of the end effector in the first coordinate system.

To move the end effector to a new location of the x-y plane the processor 78 computes the change in angles a2 and a3 and then provides output signals to move the actuators accordingly. The original angular position of the end effector is provided to the processor 78 by the position sensors. The processor moves the linkage arms an angle that corresponds to the difference between the new location and the original location of the end effector. A differential angle Δa2 corresponds to the amount of angular displacement provided by the second actuator 34, a differential angle Δa3 corresponds to the amount of angular displacement provided by the first actuator 30.

To improve the effectiveness of the system 10, the system is constructed so that the desired movement of the surgical instrument correlates to a direction relative to the image displayed by the monitor. Thus when the surgeon commands the scope to move up, the scope always appears to move in the up direction. To accomplish this result, the processor 78 converts the desired movement of the end of the endoscope in the third coordinate system to coordinates in the second coordinate system, and then converts the coordinates of the second coordinate system into the coordinates of the first coordinate system.

Referring to FIG. 2, the desired movement of the endoscope is converted from the third coordinate system to the second coordinate system by using the following transformation matrix:

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix} \quad 2)$$

where;

$\Delta x''$=the desired incremental movement of the scope along the x" axis of the third coordinate system.

$\Delta y''$=the desired incremental movement of the scope along the y" axis of the third coordinate system.

$\Delta z''$=the desired incremental movement of the scope along the z" axis of the third coordinate system.

a5=the angle between the z' axis and the scope in the y-z' plane.

a6=the angle between the z' axis and the scope in the x'-z' plane.

$\Delta x''$=the computed incremental movement of the scope along the x' axis of the second coordinate system.

$\Delta y''$=the computed incremental movement of the scope along the y' axis of the second coordinate system.

$\Delta z''$=the computed incremental movement of the scope along the z' axis of the second coordinate system.

The angles a5 and a6 are provided by position sensors located on the end effector 32. The angles a5 and a6 are shown in FIG. 2.

The desired movement of the endoscope is converted from the second coordinate system to the first coordinate system by using the following transformation matrix:

$$\begin{pmatrix} \Delta x \\ \Delta y \\ \Delta z \end{pmatrix} = \begin{pmatrix} \cos(\pi) & -sn(\pi) & 0 \\ \sin(\pi) & \cos(\pi) & 0 \\ 0 & 0 & 1 \end{pmatrix} \begin{pmatrix} \Delta x'' \\ \Delta y'' \\ \Delta z'' \end{pmatrix} \quad 3)$$

where;

$\Delta x'$=the computed incremental movement of the scope along the x' axis of the second coordinate system.

$\Delta y'$=the computed incremental movement of the scope along the y' axis of the second coordinate system.

$\Delta z'$=the computed incremental movement of the scope along the z' axis of the second coordinate system.

$\pi$=is the angle between the first linkage arm and the x axis of the first coordinate system.

$\Delta x$=the computed incremental movement of the scope along the x axis of the first coordinate system.

$\Delta y$=the computed incremental movement of the scope along the y axis of the first coordinate system.

$\Delta z$=the computed incremental movement of the scope along the z axis of the first coordinate system.

The incremental movements $\Delta x$ and $\Delta y$ are inserted into the algorithms described above for computing the angular movements ($\Delta a2$ and $\Delta a3$) of the robotic arm assembly to determine the amount of rotation that is to be provided by each electric motor. The value $\Delta z$ is used to determine the amount of linear movement provided by the linear actuator 24.

The surgical instrument is typically coupled to a camera and a viewing screen so that any spinning of the instrument about its own longitudinal axis will result in a corresponding rotation of the image on the viewing screen. Rotation of the instrument and viewing image may disorient the viewer. It is therefore desirable to maintain the orientation of the viewing image. In the preferred embodiment, the end effector has a worm gear (not shown) which rotates the surgical instrument about the longitudinal axis of the instrument. To insure proper orientation of the endoscope 16, the worm gear rotates the instrument 16 about its longitudinal axis an amount $\Delta\theta6$ to insure that the y" axis is oriented in the most vertical direction within the fixed coordinate system. $\Delta\theta6$ is computed from the following cross-products.

$\Delta\theta6$ =zi" (yo".yi")

where;

$\Delta\theta6$ =the angle that the instrument is to be rotated about the z" axis.

yo"=is the vector orientation of the y" axis when the instrument is in the first position.

yi$\Delta$=is the vector orientation of the y" axis when the instrument is in the second position.

zi"=is the vector orientation of the z" axis when the instrument is in the second position.

The vectors of the yi" and zi" axis are computed with the following algorithms.

$$[zi''] = \begin{pmatrix} \cos a6 & 0 & -\sin a6 \\ -\sin a5 \sin a6 & \cos a5 & -\sin a5 \cos a6 \\ \cos a5 \sin a6 & \sin a5 & \cos a5 \cos a6 \end{pmatrix} \begin{pmatrix} 0 \\ 0 \\ 1 \end{pmatrix}$$

$xi'' = z \times zi''$ $yi'' = zi'' \times xi''$ where;

a5=is the angle between the instrument and the z axis in the y-z plane.

a6=is the angle between the instrument and the z axis in the x-z plane.

z=is the unit vector of the z axis in the first coordinate system.

The angles a5 and a6 are provided by position sensors. The vector yo" is computed using the angles a5 and a6 of the instrument in the original or first position. For the computation of yi" the angles a5 and a6 of the second position are used in the transformation matrix. After each arm movement yo" is set to yi" and a new yi" vector and corresponding $\Delta\theta6$ angle are computed and used to re-orient the endoscope. Using the above described algorithms, the worm gear continuously rotates the instrument about its longitudinal axis to insure that the pivotal movement of the endoscope does not cause a corresponding rotation of the viewing image.

The system may have a memory feature to store desired instrument positions within the patient. The memory feature may be enabled either by voice commands or through a button on an input device such as the foot pedal. When a save command is spoken, the coordinates of the end effector in the first coordinate system are saved in a dedicated address(es) of the computer memory. When a return command is spoken, the processor retrieves the data stored in memory and moves the end effector to the coordinates of the effector when the save command was enabled.

The memory feature allows the operator to store the coordinates of the end effector in a first position, move the end effector to a second position and then return to the first position with a simple command. By way of example, the surgeon may take a wide eye view of the patient from a predetermined location and store the coordinates of that location in memory. Subsequently, the surgeon may manipulate the endoscope to enter cavities, etc. which provide a more narrow view. The surgeon can rapidly move back to the wide eye view by merely stating "AESOP return to one".

In operation, the user provides spoken words to the microphone. The phrase recognizer 86 matches the user's speech with stored words and provides matched electronic words to the processor 78. The processor performs a grammar process to determine whether the spoken words are robot commands. If the words are commands, the computer energizes the actuators and moves the endoscope, accordingly. The system also allows the user to control the movement of the endoscope with a foot pedal if voice commands are not desired.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art:

What is claimed is:

1. A voice recognition system for use with a surgical instrument, the system comprising:
    a processor coupled to a microphone and to a memory, the processor having a first state and a second state;
    wherein the microphone receives a plurality of spoken surgical instructions, each of the spoken surgical instructions including a spoken qualifier and a spoken command, the plurality of spoken surgical instructions including a first surgical instruction having a first spoken qualifier and a first spoken command;
    wherein the memory stores a first plurality of allowable commands associated with the second state of the processor; and
    wherein in the first state, the processor is configured to:
        receive the first surgical instruction and determine if the first spoken qualifier included in the first surgical instruction satisfies a first condition;
        if the first spoken qualifier satisfies the first condition, then advance to the second state; and
        if the first spoken qualifier does not satisfy the first condition, then remain in the first state; and
    wherein in the second state, the processor is configured to:
        determine whether the first spoken command included in the first surgical instruction is among the first plurality of allowable commands associated with the second state; and
        if the first spoken command is among the first plurality of allowable commands, then transmit a first command signal to the surgical instrument in response to the first spoken command being among the first plurality of allowable commands.

2. The voice recognition system of claim 1, wherein the surgical instrument includes an endoscope configured to be coupled to a monitor, the processor configured to be coupled to the endoscope so as to alter an image from the endoscope that is shown on the monitor.

3. The voice recognition system of claim 2, the surgical instrument including a robotic arm supporting the endoscope, a distal end of the endoscope including a tip defining a viewing coordinate frame, wherein the processor is configured to calculate transformations between the viewing coordinate frame and a coordinate frame of the robotic arm, and the first command signal includes motor signals derived from the transformations so that the tip moves in an internal surgical site to effect an instructed change in the image shown on the monitor.

4. The voice recognition system of claim 1, wherein:
    the processor is configured to be coupled to the surgical instrument.

5. The voice recognition system of claim 1, wherein the plurality of spoken surgical instructions includes a second instruction having a second spoken qualifier and a second spoken command, the memory operable to store a second plurality of allowable commands, the processor operable to change to a third state in response to the second spoken qualifier satisfying a second condition, the processor in the third state configured to determine whether the second spoken command is among the second plurality of allowable commands associated with the third state, the processor operable to generate a second command signal in response to the second spoken command being among the second plurality of allowable commands.

6. The voice recognition system of claim 5, wherein the processor has a fourth state, the processor operable to change to the fourth state in response to the second spoken command, the processor in the fourth state operable to accept a third plurality of allowable commands stored in the memory and associated with the fourth state.

7. The voice recognition system of claim 1, further comprising a speaker coupled to the processor for generating audible messages to a surgeon regarding operation of the system.

8. The voice recognition system of claim 7, wherein the audible messages include audible feedback indicating successful receipt of each spoken surgical instruction.

9. The voice recognition system of claim 8, wherein the audible messages include synthesized voice messages.

10. The voice recognition system of claim 1, wherein the microphone accepts a spoken stop command, and the processor is configured to transmit a stop command signal to the surgical instrument in response to the spoken stop command without an associated spoken qualifier.

11. The voice recognition system of claim 10, wherein the stop command signal from the processor is configured to inhibit potential injury to the patient that might otherwise be inflicted by the surgical instrument.

12. The voice recognition system of claim 1, wherein:
    determining whether the first spoken command is among the first plurality of allowable commands includes comparing the first spoken command to at least one of the allowable commands in the first plurality of allowable commands.

13. A method comprising:
    receiving a spoken surgical instruction, the spoken surgical instruction comprising a verbal qualifier and a verbal control command, wherein the verbal qualifier precedes the verbal control command;
    determining whether the verbal qualifier matches an expected qualifier associated with a medical device;
    if the verbal qualifier matches the expected qualifier, then determining whether the verbal control command is among one or more predefined commands from a library of multiple predefined commands; and
    providing an output command signal that corresponds to the verbal control command to the medical device only if the verbal qualifier matches the expected qualifier and the verbal control command is among the one or more predefined commands.

14. The method of claim 13, further comprising:
providing audio or visual feedback after receiving the verbal control command.

15. The method of claim 13, wherein:
the expected qualifier includes a name of the medical device.

16. The method of claim 13, wherein:
the medical device comprises a robotic arm.

17. The method of claim 13, wherein:
determining whether the verbal qualifier matches the expected qualifier includes comparing the verbal qualifier to the expected qualifier; and
determining whether the verbal control command is among the one or more predefined commands includes comparing the verbal control command to at least one of the one or more predefined commands.

18. A voice recognition system for use with a surgical instrument, the system comprising:
a microphone for inputting a plurality of spoken surgical instructions, each of the spoken surgical instructions including a spoken qualifier and a spoken command, the plurality of spoken surgical instructions including a first instruction comprising a first spoken qualifier and a first spoken command, wherein the first spoken command comprises a first portion and a second portion;
a memory for storing a first plurality of allowable commands and a second plurality of allowable compounds; and
a processor coupled to the microphone and the memory, the processor having a first state, a second state, and a third state, wherein the first plurality of allowable commands are associated with the second state, wherein the second plurality of allowable commands are associated with the third state, and wherein the processor is configured to:
in the first state, in response to the first spoken qualifier matching an expected qualifier, advance to the second state;
in the second state, determine if the first portion of the first spoken command is among the first plurality of allowable commands associated with the second state and to advance to the third state in response to the first portion being among the first plurality of allowable commands;
in the third state, determine if the second portion of the first spoken command is among the second plurality of allowable commands associated with the third state; and
in response to the second portion of the first spoken command being among the second plurality of allowable commands provide a first command signal to the surgical instrument corresponding to the first spoken command.

19. A method for controlling a surgical instrument, the method comprising:
in a first state, receiving a plurality of spoken surgical instructions, each of the spoken surgical instructions including a spoken qualifier and a spoken command, the plurality of spoken surgical instructions including a first surgical instruction having a first spoken qualifier and a first spoken command;
determining if the first spoken qualifier included in the first surgical instruction satisfies a first condition;
if the first spoken qualifier satisfies the first condition, then advancing to a second state;
in the second state, determining whether the first spoken command included in the first surgical instruction is among a plurality of allowable commands associated with the second state; and
if the first spoken command is among the first plurality of allowable commands, then transmitting a first command signal to the surgical instrument in response to the first spoken command being among the plurality of allowable commands.

20. The voice recognition system of claim 1, wherein the first plurality of allowable commands comprises a save command.

21. The voice recognition system of claim 1, wherein the first plurality of allowable commands comprises a return command.

22. The voice recognition system of claim 1, wherein the first plurality of allowable commands comprises a track instrument command.

23. The voice recognition system of claim 1, wherein the first plurality of allowable commands comprises a track head command.

24. A method comprising:
receiving a first spoken surgical instruction, the first spoken surgical instruction comprising a verbal qualifier and a first verbal control command, the verbal qualifier preceding the first verbal control command;
determining whether the verbal qualifier matches an expected qualifier;
if the verbal qualifier matches the expected qualifier, then determining whether the first verbal control command is among one or more predefined commands from a first library of multiple predefined commands;
providing a first output command signal that corresponds to the first verbal control command to a medical device only if the verbal qualifier matches the expected qualifier and the first verbal control command is among the predefined commands in the first library;
receiving a second spoken surgical instruction, the second spoken surgical instruction comprising the verbal qualifier and a second verbal control command, the verbal qualifier preceding the second verbal control command;
determining whether the verbal qualifier matches the expected qualifier;
if the verbal qualifier matches the expected qualifier, then determining whether the second verbal control command is among one or more predefined commands from a second library of multiple predefined commands; and
providing a second output command signal that corresponds to the second verbal control command to the medical device only if the verbal qualifier matches the expected qualifier and the second verbal control command is among the predefined commands in the second library.

25. A method comprising:
receiving a spoken surgical instruction, the spoken surgical instruction comprising a verbal qualifier and a verbal control command comprising a first part and a second part, the verbal qualifier preceding the verbal control command;
determining whether the verbal qualifier matches an expected qualifier;
if the verbal qualifier matches the expected qualifier, then determining whether the first part of the verbal control command is among one or more predefined commands from a first library of multiple predefined commands;
if the first part of the verbal control command is among the predefined commands in the first library, then determining whether the second part of the verbal control command is among one or more predefined commands in a second library of multiple predefined commands; and providing an output command signal to a medical device, wherein the output command signal corresponds to the first and second parts of the verbal control command only if: the verbal qualifier matches the expected qualifier, the first part of the verbal control command is among the predefined commands in the first library, and the second part of the verbal control command is among the predefined commands in the second library.

26. The voice recognition system of claim 1, wherein:

the plurality of spoken surgical instructions includes a second instruction including the first spoken qualifier and a second spoken command including a first part and a second part;

the memory is further operable to store a second plurality of allowable commands associated with a third state of the processor;

the processor is further operable in the second state to:
determine whether the first part of the second spoken command is among the first plurality of allowable commands associated with the second state;
if the first part is among the first plurality of allowable commands, then advance to the third state and determine whether the second part of the second spoken command is among the second plurality of allowable commands associated with the third state; and
if the second part is among the second plurality of allowable commands, then transmit a second command signal to the surgical instrument in response to the second spoken command.

* * * * *